US007541180B2

(12) United States Patent
Valiante (10) Patent No.: US 7,541,180 B2
(45) Date of Patent: Jun. 2, 2009

(54) NUCLEIC ACID VECTORS FOR IMMUNIZATION

(75) Inventor: Nicholas Valiante, Fremont, CA (US)

(73) Assignee: Novartis Vaccines and Diagnostics SRL, Siena (IT)

( * ) Notice: Subject to any disclaimer, the term of this patent is extended or adjusted under 35 U.S.C. 154(b) by 201 days.

(21) Appl. No.: 10/479,649

(22) PCT Filed: May 30, 2002

(86) PCT No.: PCT/IB02/03105

§ 371 (c)(1),
(2), (4) Date: Dec. 1, 2003

(87) PCT Pub. No.: WO02/098456

PCT Pub. Date: Dec. 12, 2002

(65) Prior Publication Data

US 2004/0147721 A1 Jul. 29, 2004

(30) Foreign Application Priority Data

Jun. 6, 2001 (GB) .................................. 0113798.3

(51) Int. Cl.
*C12N 15/00* (2006.01)
*C07H 21/02* (2006.01)
*C07H 21/00* (2006.01)
(52) U.S. Cl. .................... 435/320.1; 536/23.1; 435/455; 514/44
(58) Field of Classification Search .................. None
See application file for complete search history.

(56) References Cited

FOREIGN PATENT DOCUMENTS

WO WO 98/44129 10/1998
WO WO 01/02440 1/2001

OTHER PUBLICATIONS

Black et al., Molecular Cell, 2007, 25: 309-322.*
Blazer et al., J. Immunol., 1996, 157: 3250-3259.*
Wallet et al., 2005, Clinical Medicine and Research, 3: 166-175.*
NCBI record Accession No. Q69091 (2008).*
Boyle et al., "Enhanced Responses to a DNA Vaccine Encoding a Fusion Antigen That is Directed to Sites of Immune Induction," Nature 392:408-411 (1998).
Chaplin et al, "Targeting Improves the Efficacy of a DNA Vaccine Against Corynebacterium Pseudotuberculosis in Sheep," Infection and Immunity 67:6434-6438 (1999).
Choo et al., "Vaccination of Chimpanzees Against Infection by the Hepatitis C Virus," Proc. Natl. Acad. Sci. USA 91:1294-1298 (1994).
Deliyannis et al., "A Fusion DNA Vaccine That Targets Antigen-Presenting Cells Increases Protection From Viral Challenge," Proc. Natl. Acad. Sci. USA 97(12):6676-6680 (2000).
Donnelly et al., "DNA Vaccines," Annu. Rev. Immunol 15:617-648 (1997).

Fuller et al., "Enhancement of Immunodeficiency Virus-Specific Immune Responses in DNA-Immunized Rhesus Macaques," Vaccine 15(8):924-925 (1997).
Greene et al., "Covalent Dimerization of CD28/CTLA-4 and Oligomerization of CD80/CD86 Regulate T Cell Costimulatory Interactions," J. Biol. Chem. 271(43):26762-26771 (1996).
Habersetzer et al., "Isolation of Human Monoclonal Antibodies (HMABS) Directed at Conformational Determinants of the Hepatitis C Virus (HCV) E2 Envelope Protein," Hepatology 24(4):381A (1996).
Hartikka et al., "Am Improved Plasmid DNA Expression Vector for Direct Injection Into Skeletal Muscle," Hum. Gene Ther. 7:1205-1217 (1996).
Heile et al., "Evaluation of Hepatitis C Virus Glycoprotein E2 for Vaccine Design: an Endoplasmic Reticulum-Retained Recombinant Protein is Superior to Secreted Recombinant Protein and DNA-Based Vaccine Candidates," J. Virol. 74(15):6885-6892 (2000).
Kwissa et al., "Efficient Vaccination by Intradermal or Intramuscular Inoculation of Plasmid DNA Expressing Hepatitis B Surface Antigen Under Desmin Promoter/Enhancer Control," Vaccine 18:2337-2344 (2000).
Leitner et al., "DNA and RNA-Based Vaccines: Principles, Progress and Prospects," Vaccine 18:765-777 (2000).
Lew et al., "Site-Directed Immune Responses in DNA Vaccines Encoding Ligand-Antigen Fusions," Vaccine 18:1681-1685 (2000).
Linsley et al., "T-Cell Antigen CD28 Mediates Adhesion With B Cells by Interacting With Activation Antigen B7/BB-1," Proc. Natl. Acad. Sci. USA 87:5031-5035 (1990).
Matthias et al., "Two Pairs of Oppositely Charged Amino Acids From JUN and FOS Confer Heterodimerization to GCN4 Leucine Zipper," The Journal of Biological Chemistry 269(23):16247-16253 (1994).
Pardoll et al., "Exposing the Immunology of Naked DNA Vaccines," Immunity 3:165-169 (1995).
Rosa et al., "A Quantitative Test to Estimate Neutralizing Antibodies to the Hepatitis C Virus: Cytofluorimetric Assessment of Envelope Glycoprotein 2 Binding to Target Cells," Proc. Natl. Acad. Sci. USA 93:1759-1763 (1996).
Sato et al., "Immunostimulatory DNA Sequences Necessary for Effective Intradermal Gene Immunization," Science 273:352-354 (1996).
Schouten et al., "The C-Terminal KDEL Sequence Increases the Expression Level of a Single-Chain Antibody Designed to be Targeted to Both the Cytosol and the Secretory Pathway in Transgenic Tobacco", Plant Molecular Biology, 30:781-793 (1996).

(Continued)

*Primary Examiner*—Ilia Ouspenski
(74) *Attorney, Agent, or Firm*—Helen Lee; Otis Littlefield; Robert Gorman (57) ABSTRACT

A dimeric protein comprising a first fusion protein and a second fusion protein, wherein the first fusion protein comprises a targeting domain, a leucine zipper domain, and an antigen; and wherein the second fusion protein comprises a targeting domain, a leucine zipper domain, and optionally an antigen. Nucleic acid vectors encoding proteins of the invention are provided, particularly for use in nucleic acid vaccination.

17 Claims, 2 Drawing Sheets

OTHER PUBLICATIONS

Siemoneit et al., "Human Monoclonal Antibodies for the Immunological Characterization of a Highly Conserved Protein Domain of the Hepatitis C Virus Glycoprotein E1," Clinical and Experimental Immunology 101:278-283 (1995).

Takeda et al., "GPI-Anchor Biosynthesis," Trends in Biochemical Sciences, 20(9):367-371 (1995).

Ulivieri et al., "Generation of a Monoclonal Antibody to a Defined Portion of the Helicobacter Pylori Vacuolating Cytotoxin by DNA Immunization," J. Biotech 51:191-194 (1996).

Wang et al., "Induction of Antigen-Specific Cytotoxic T Lymphocytes in Humans by a Malaria DNA Vaccine," Science 282:476-480 (1998).

Yew et al., "Optimization of Plasmid Vectors for High-Level Expression in Lung Epithelial Cells," Hum. Gene Ther. 8:575-584 (1997).

Armand et al., "Targeted Expression of HTLV-1 Envelope Proteins in Muscle by DNA Immunization of Mice," Vaccine, 18:2212-2222 (2000).

Barnhart et al., "Enhancer and Promoter Chimeras in Plasmids Designed for Intramuscular Injection: a Comparative in vivo and in vitro Study," Human Gene Therapy, 9:2545-2553 (1998).

* cited by examiner

SEQUENCE LISTING

```
<160> NUMBER OF SEQ ID NOS: 21

<210> SEQ ID NO 1
<211> LENGTH: 71
<212> TYPE: DNA
<213> ORGANISM: Artificial Sequence
<220> FEATURE:
<223> OTHER INFORMATION: Primer msc1

<400> SEQUENCE: 1
ggccgcacgc gtactagtgg gcccgggcgt acgcttaaga atcgatatcg gtaccagatc    60
tgaattcggc c                                                         71

<210> SEQ ID NO 2
<211> LENGTH: 71
<212> TYPE: DNA
<213> ORGANISM: Artificial Sequence
<220> FEATURE:
<223> OTHER INFORMATION: Primer msc2

<400> SEQUENCE: 2
```

-continued ggccggccga attcagatct ggtaccgata tcgattctta agcgtacgcc cgggcccact    60
agtacgcgtg c                                                          71

<210> SEQ ID NO 3
<211> LENGTH: 31
<212> TYPE: DNA
<213> ORGANISM: Artificial Sequence
<220> FEATURE:
<223> OTHER INFORMATION: Primer ori1

<400> SEQUENCE: 3
atcgtagtcg acgcgttgct ggcgtttttc c                                    31

<210> SEQ ID NO 4
<211> LENGTH: 33
<212> TYPE: DNA
<213> ORGANISM: Artificial Sequence
<220> FEATURE:
<223> OTHER INFORMATION: Primer ori2

<400> SEQUENCE: 4
atcgtaaagc ttatccctta acgtgagttt tcg                                  33

<210> SEQ ID NO 5
<211> LENGTH: 30
<212> TYPE: DNA
<213> ORGANISM: Artificial Sequence
<220> FEATURE:
<223> OTHER INFORMATION: Primer asd1

<400> SEQUENCE: 5
tacgcctgca gggatcttcc ctaaatttaa                                      30

<210> SEQ ID NO 6
<211> LENGTH: 30
<212> TYPE: DNA
<213> ORGANISM: Artificial Sequence
<220> FEATURE:
<223> OTHER INFORMATION: Primer asd2

<400> SEQUENCE: 6
tacgcaagct tttccaattca acatcaggta                                     30

<210> SEQ ID NO 7
<211> LENGTH: 32
<212> TYPE: DNA
<213> ORGANISM: Artificial Sequence
<220> FEATURE:
<223> OTHER INFORMATION: Primer iss1

<400> SEQUENCE: 7
agctagctag caacgtcagg aacgtcatgg at                                   32

<210> SEQ ID NO 8
<211> LENGTH: 30
<212> TYPE: DNA
<213> ORGANISM: Artificial Sequence
<220> FEATURE:
<223> OTHER INFORMATION: Primer iss2

<400> SEQUENCE: 8
agctatccat gacgttcgac gttgctagct                                      30

<210> SEQ ID NO 9
<211> LENGTH: 20

```
<212> TYPE: DNA
<213> ORGANISM: Artificial Sequence
<220> FEATURE:
<223> OTHER INFORMATION: Primer ctla41

<400> SEQUENCE: 9
gccatacagg tgacccaacc                                              20

<210> SEQ ID NO 10
<211> LENGTH: 18
<212> TYPE: DNA
<213> ORGANISM: Artificial Sequence
<220> FEATURE:
<223> OTHER INFORMATION: Primer ctla42

<400> SEQUENCE: 10
gtcagaatcc gggcatgg                                                18

<210> SEQ ID NO 11
<211> LENGTH: 49
<212> TYPE: DNA
<213> ORGANISM: Artificial Sequence
<220> FEATURE:
<223> OTHER INFORMATION: Primer fus1

<400> SEQUENCE: 11
gaaatccaat gcccgattca gaagagccag atctgccata caggtgacc              49

<210> SEQ ID NO 12
<211> LENGTH: 46
<212> TYPE: DNA
<213> ORGANISM: Artificial Sequence
<220> FEATURE:
<223> OTHER INFORMATION: Primer fus2

<400> SEQUENCE: 12
tgtttcatgc gtccaccgcc tcctccatcg atgtcagaat ccgggc                 46

<210> SEQ ID NO 13
<211> LENGTH: 44
<212> TYPE: DNA
<213> ORGANISM: Artificial Sequence
<220> FEATURE:
<223> OTHER INFORMATION: Primer fus3

<400> SEQUENCE: 13
tgtggagcag tcttcgtttc gcccagccag gaaatccatg cccg                   44

<210> SEQ ID NO 14
<211> LENGTH: 50
<212> TYPE: DNA
<213> ORGANISM: Artificial Sequence
<220> FEATURE:
<223> OTHER INFORMATION: Primer fus4

<400> SEQUENCE: 14
ttttcgaaag aagctcttca actttatctt ccagctgttt catgcggtcc             50

<210> SEQ ID NO 15
<211> LENGTH: 45
<212> TYPE: DNA
<213> ORGANISM: Artificial Sequence
<220> FEATURE:
<223> OTHER INFORMATION: Primer fus5

<400> SEQUENCE: 15
```

-continued aagagagggc tctgctgtgt gctgctgctt gtggagcagt cttcg        45

<210> SEQ ID NO 16
<211> LENGTH: 58
<212> TYPE: DNA
<213> ORGANISM: Artificial Sequence
<220> FEATURE:
<223> OTHER INFORMATION: Primer fus6

<400> SEQUENCE: 16
tttttgaggc gcgcaacttc attttcgagg tggtggtagt ttttcgaaag aaagaagc        58

<210> SEQ ID NO 17
<211> LENGTH: 45
<212> TYPE: DNA
<213> ORGANISM: Artificial Sequence
<220> FEATURE:
<223> OTHER INFORMATION: Primer fus8

<400> SEQUENCE: 17
taaatcatgg ccggccgcca tggatgcaat gaagagaggc tctgc        45

<210> SEQ ID NO 18
<211> LENGTH: 44
<212> TYPE: DNA
<213> ORGANISM: Artificial Sequence
<220> FEATURE:
<223> OTHER INFORMATION: Primer fus8

<400> SEQUENCE: 18
cctccaccac cgcgttcacc aacaacaagt tttttgaggc gcgc        44

<210> SEQ ID NO 19
<211> LENGTH: 44
<212> TYPE: DNA
<213> ORGANISM: Artificial Sequence
<220> FEATURE:
<223> OTHER INFORMATION: Primer fus9

<400> SEQUENCE: 19
cttccaacta gtcctgaatt cccgggcccg cttccaacta gtcc        44

<210> SEQ ID NO 20
<211> LENGTH: 48
<212> TYPE: DNA
<213> ORGANISM: Artificial Sequence
<220> FEATURE:
<223> OTHER INFORMATION: Primer fus10

<400> SEQUENCE: 20
atagtttagc ggccgcttaa ctattcacta taagcttcca actagtcc        48

Figure 1:
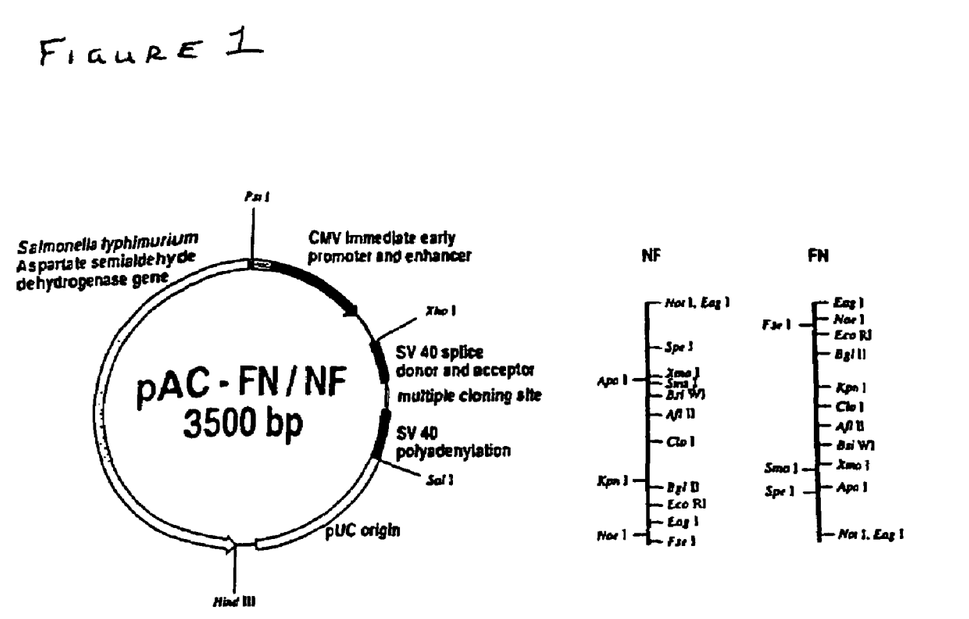
FIG. 1: The DNA vaccination vector pAC-FN/NF (starting point vector)
Figure 2:
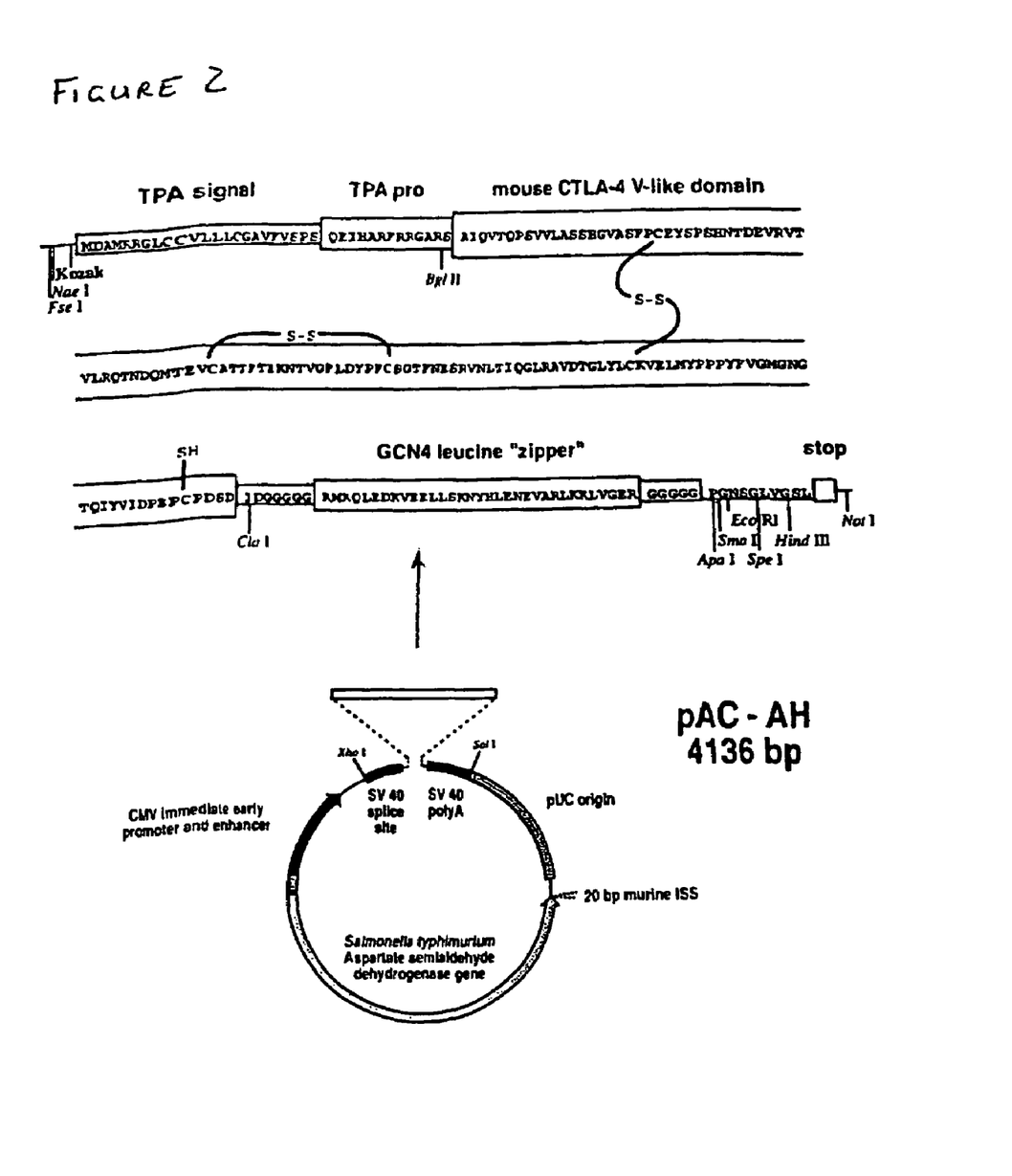
FIG. 2: The DNA vaccination vector pAC-AH (final vector) encoding the amino acid sequence of SEQ ID NO:21.

<210> SEQ ID NO 21
<211> LENGTH: 216
<212> TYPE: PRT
<213> ORGANISM: Artificial Sequence
<220> FEATURE:
<223> OTHER INFORMATION: Sequence in Fig 2

<400> SEQUENCE: 21

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Ala Ile Gln Val Thr Gln Pro Ser Val Val Leu Ala

-continued

```
                35                  40                  45
Ser Ser His Gly Val Ala Ser Phe Pro Cys Glu Tyr Ser Pro Ser His
        50                  55                  60

Asn Thr Asp Glu Val Arg Val Thr Val Leu Arg Gln Thr Asn Asp Gln
 65              70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Pro Tyr Phe Val Gly Met Gly
        130                 135                 140

Asn Gly Thr Gln Ile Tyr Val Ile Asp Pro Glu Pro Cys Pro Asp Ser
145                 150                 155                 160

Asp Ile Asp Gly Gly Gly Gly Arg Met Lys Gln Leu Glu Asp Lys
                165                 170                 175

Val Glu Glu Leu Leu Ser Lys Asn Tyr His Leu Glu Asn Glu Val Ala
            180                 185                 190

Arg Leu Lys Lys Leu Val Gly Glu Arg Gly Gly Gly Gly Gly Pro Gly
        195                 200                 205

Asn Ser Gly Leu Val Gly Ser Leu
    210                 215
```

NUCLEIC ACID VECTORS FOR IMMUNIZATION

This application is a §371 National Phase filing of PCT/IB02/03105, filed May 30, 2002, which claims the benefit of GB 0113798.3, filed Jun. 6, 2001, from which applications priority is claimed pursuant to the provisions of 35 U.S.C. §§ 119/120 and which applications are incorporated by reference herein in their entireties.

All documents cited herein are incorporated by reference in their entirety

TECHNICAL FIELD

This invention is in the field of vaccination, and in particular antigens and vectors useful for nucleic acid vaccination. The vectors can be used to stimulate a specific immune response against one or more antigens.

BACKGROUND ART

Immunization with nucleic acids has the potential to circumvent many of the problems associated with protein vaccines.

Nucleic acid vaccines are relatively inexpensive to produce, overcoming the high costs of production and difficulties in purification associated with the preparation of soluble protein antigens. Furthermore, immunization with protein antigen is associated with problems of incorrect folding and poor induction of cell-mediated immunity. In contrast, nucleic acid immunization generates correctly folded conformational determinants and maximises the presentation of processed antigenic determinants on MHC molecules, eliciting both humoral and cell-mediated immunity. Nucleic acid vaccination therefore holds great promise for infectious disease prophylactics and immunotherapy.

The efficacy of DNA vaccination has been successfully demonstrated in animal models for a wide range of pathogens (Pardoll, 1995; Donnelly, 1997). However, there are still major practical and theoretical obstacles to overcome before the potential of these vaccines can be realised. Most animal model studies were carried out in rodents and it subsequently became clear that in larger animals, in particular primates and humans, DNA vaccination has limited efficacy (Fuller, 1997; Wang, 1998). Although DNA vaccines typically elicit good cell-mediated immunity, they elicit poor humoral immunity, leading some to conclude that nucleic acid vaccines will not replace conventional protein vaccines.

Several strategies to improve the immunogenicity of DNA vaccines and manipulate the immune response have been developed, such as the use of various viral, eukaryotic and combined promoters (Donnelly, 1997; Barnhart, 1998; Armand, 2000; Kwissa, 2000), the improvement of transgene expression (Hartikka, 1996; Yew, 1997), the addition of immunostimulatory sequences into the vector backbone which act in vivo as a T helper 1 enhancing adjuvant (Sato, 1996), or the co-expression of costimulatory molecules, such as cytokines or chemokines (Leitner, 2000).

However, none of these strategies has been particularly successful and there remains a need to increase the immunogenicity of nucleic acid vaccines and enhance humoral responses elicited by nucleic acid vaccines. An object of the invention is to provide nucleic acid vaccines which elicit good humoral responses, making them a viable alternative to conventional vaccines.

An approach suggested by Boyle et al involves targeting antigen to sites of immune induction by vaccination with DNA encoding the antigen as a CTLA-4 fusion protein (Boyle, 1998). CTLA-4 is expressed on activated T cells and binds to the surface receptor B7-1 and B7-2 of antigen-presenting cells (APCs), which are potent initiators of immune responses (Linsley, 1990). Deliyannis et al demonstrated that this approach enhanced the speed and magnitude of the immune response against a viral antigen in mice. Vaccinated mice were found to have significantly reduced viral titres when faced with viral challenge (Deliyannis et al, 2000). Chaplin et al found that targeting improved the efficacy of a DNA vaccine against *Corynebacterium* in sheep (Chaplin et al, 1999).

These workers used vaccination vectors comprising a plasmid encoding an antigen fused to a CTLA-4-human immunoglobulin structure. High avidity binding of CTLA-4 to its receptor requires CTLA-4 dimerization (Greene, 1996), and this dimerization is also critical for the observed enhancement of the immune response (Lew, 2000). As a dimerization moiety, the authors used either the hinge and heavy chain constant domains of human IgG1, or only the hinge regions of human IgG3.

However, this approach also results in antigen dimerization which can have negative effects on the quality of the immune response. For example, monomers but not dimers of recombinant HCV glycoprotein E2, expressed in chinese hamster ovary cells, have the biological activity required to elicit a good antibody response (Heile, 2000). Recombinant E2 protein expressed in mammalian cells tends to form aggregates, which are stabilised by disulphide bonds. It is likely that such aggregates will also form when E2 is forced to be in close vicinity with a copy of itself in the context of a dimerized fusion protein. Thus, an object of the invention is the provision of more sophisticated nucleic acid vectors which allow the antigen to be targeted to the preferred cells in a monomeric state.

Similarly, there is a need for nucleic acid vectors that would allow the homodimerization or heterodimerization of the targeting moiety whilst allowing antigen heterodimerization. Taking HCV as an example again, E2 heterodimerizes with E1 in vitro. When vaccinated with recombinant E1-E2 heterodimers, chimpanzees develop high titres of anti-E2 antibodies in serum and are completely protected from subsequent challenge with the homologous virus (Choo, 1994; Rosa, 1996). An object of the invention is to circumvent the inherent difficulties associated with producing E1-E2 heterodimers by providing a nucleic acid vaccine encoding an E1-E2 heterodimer such that the heterodimer is targeted to APCs. A further object of the invention is to provide nucleic acid vaccines which stimulate effective cell-mediated and humoral immune responses against more than one antigen Monoclonal antibodies are invaluable research tools for various techniques such as ELISA, immunoblots, immunohistology and cytofluorimetry and are often the key to the characterization of protein structure, function and purification. They permit efficient purification by affinity chromatography and allow functional characterization by blocking binding or active sites. Traditionally, the production of specific polyclonal and monoclonal antibodies has required the purification and injection of significant amounts of protein from tissues or fluids for immunization, or the injection of mammalian cell clones expressing certain markers, followed by extensive screening procedures. It is now possible to obtain information about a protein from its cloned sequence without ever having purified it, and recombinant forms of the protein can be expressed and purified from cells or supernatent in various systems. However, this remains a difficult undertaking and the process of obtaining recombinant protein in native conformation in sufficient yield and purity for immunization and screening still remains a limiting step in the path towards obtaining antibodies. Immunizing mice or other small animals with nucleic acid encoding the protein has been suggested as a way of overcoming these problems (Ulvieri, 1996).

However, current nucleic acid immunization vectors do not provide sufficient yields to make this method viable. An object of the invention is the provision of nucleic acid vectors which allow increased antibody yields to be obtained.

DISCLOSURE OF THE INVENTION

According to a first aspect of the invention, there is provided a dimeric protein comprising a first fusion protein and a second fusion protein,
wherein the first fusion protein comprises
  (i) a targeting domain,
  (ii) a leucine zipper domain, and
  (iii) an antigen;
and wherein the second fusion protein comprises
  (i) a targeting domain
  (ii) a leucine zipper domain, and
  (iii) optionally an antigen.

The targeting domain in the first and the second fusion proteins may be fused to either the C-terminal or the N-terminal of the leucine zipper domain with the antigen domain fused to the other terminal of the leucine zipper domain. The order of fusion in the first and the second fusion proteins is the same. Hence if the targeting domain of the first fusion protein is fused to the C-terminal of the leucine zipper domain with the antigen fused to the N-terminal of the leucine zipper domain, the targeting domain of the second fusion protein is also fused to the C-terminal of the leucine zipper domain with an antigen optionally fused to the N-terminal of the leucine zipper domain. Similarly, if the targeting domain of the first fusion protein is fused to the N-terminal of the leucine zipper domain with the antigen fused to the C-terminal of the leucine zipper domain, the targeting domain of the second fusion protein is also fused to the N-terminal of the leucine zipper domain with an antigen optionally fused to the C-terminal of the leucine zipper domain.

The dimeric protein may be targeted to antigen presenting cells (APCs), such as MHC II+ B-cells, dendritic cells and monocyte macrophages. The dimeric protein can bind to proteins on the surface of the APCs via the targeting proteins. Binding of the dimeric protein to APCs targets the antigen(s) in the dimeric protein to those cells, stimulating an enhanced immune response to the antigen(s).

The targeting domains in the first and second fusion proteins may be the same or different. Where the targeting domains are the same, preferably they will be CTLA4 or a fragment thereof, most preferably the V-like domain. As an alternative, the targeting domain can be an antibody which will bind to a protein on the surface of the APC. Recently, a reporter antigen linked to a monoclonal antibody that binds to the CD11c molecule on the surface of murine dendritic cells was used for immunisation. The study demonstrated that a single-step delivery of small amounts of protein antigen targeted to dendritic cells in vivo can give very rapid and high antibody responses and strongly supports the general concept of targeting antigens to receptors. In such a situation, the targeting protein in one fusion protein can be the light chain of the antibody and the targeting protein in the other fusion protein can be the heavy chain of the antibody.

The term "leucine zipper domain" is used to denote a commonly recognised dimerisation domain characterised by the presence of a leucine residue every seventh residue in a stretch of approximately 35 residues. Leucine zipper domains form dimers held together by an alpha-helical coiled coil. A coiled coil has 3.5 residues per turn, which means that every seventh residue occupies an equivalent position with respect to the helix axis. The regular array of leucines inside the coiled coil stabilizes the structure by hydrophobic and Van der Waals interactions.

Leucine zipper domains in first fusion protein and the second fusion protein may be the same or different. The leucine zipper domains may be isolated from natural proteins known to contain such domains, such as transcription factors. Preferably, where both leucine zipper domains are the same, they are from the transcription factor GCN4. Alternatively, where the leucine zipper domains are different, one leucine zipper domain comes from the transcription factor fos and the second from the transcription factor jun. The leucine zipper domains may also be designed and synthesised artificially, using standard techniques for synthesis and design known in the art.

The antigens of the first and second fusion proteins may be the same or different. If they are the same, the antigen will be targeted to APCs in homodimeric form or, if it does not form a dimer, in dual monomeric form. If they are different, the two antigens can be targeted to APCs in heterodimeric form or, if they do not form a dimer, in separate monomeric form. Heterodimeric antigens may be used advantageously to promote an immune response against antigens which is correctly folded only in the context of a heterodimer. Alternatively, an immune response against both antigens may be stimulated. Finally, only one of the fusion proteins need include an antigen, such that the antigen is targeted to APCs as a single monomer. The dimeric proteins of the invention therefore enable the antigen(s) to be targeted to APCs in single monomeric, dual monomeric, homodimeric, heterodimeric or separate monomeric form.

The antigen or antigens may be any protein. Preferably, the antigens are selected from tumour antigens, bacterial antigens, viral antigens or parasitic antigens. Examples of antigens which may be employed include A/B toxins such as cholera toxin or *E. coli* heat labile toxin, Hepatitis C antigens (e.g. hepatitis B surface antigen), pertussis toxin, viral splice proteins and Hepatitis C antigens. Preferably, viral antigens are HCV antigens. Most preferably, the antigen in the first fusion protein is the HCV E1 protein and the antigen in the second fusion protein is the HCV E2 protein.

The fusion proteins may further comprise linker sequences, such as glycine linkers, between the targeting protein and the leucine zipper domain and/or the leucine zipper domain and the antigen.

According to a further aspect of the invention there is provided a monomeric protein comprising:
  (i) a targeting domain
  (ii) a leucine zipper domain and
  (iii) an antigen.

Two such proteins can dimerise via their leucine zipper domains to form a dimeric protein. The monomeric proteins which dimerise to form a dimeric protein may be the same or they may be different. The dimeric proteins formed by the dimerisation of two such monomeric proteins include the dimeric proteins described above.

According to a further aspect of the invention, there is provided a nucleic acid vector encoding a protein of the invention. The vector may encode one or more fusion proteins. Where the vector encodes one fusion protein, this can be itself used for the expression of homodimers, or can be used in combination with a different second vector for the expression of heterodimers. Where the vector encodes two fusion proteins, dimers can be expressed using a single vector.

The invention also provides a kit comprising two or more vectors of the invention.

Where the nucleic acid vector is a DNA vector, the vector will comprise a promoter. A "promoter" is a region of DNA that signals RNA polymerase binding and the initiation of transcription. The promoters used in the vectors of the invention must be functional in mammalian cells. That is, they must be able to direct efficient transcription of the fusion proteins encoded by the vector. Preferably, the promoters employed in the vectors of the invention are selected from the group consisting of a CMV promoter or an alphavirus promoter In the case of a kit comprising two monomeric vectors, the promoters for the two monomeric proteins encoded by the two vectors may be the same or different.

Where the vector encodes two fusion proteins, these may be translated from separate transcripts, or the transcript may comprise an internal ribosome entry site (IRES; Ramos, 1999) to enable translation of the two fusion proteins from a single transcript.

Optionally, the nucleic vector(s) of the invention may further comprise sequences encoding proteins that promote secretion of the monomeric or dimeric proteins they encode or target them to specific intracellular compartments. For example, the human tissue-type plasminogen activator (TPA) signal/pro sequence (Pennica, 1983) can be fused to the N-terminus of the targeting protein, such as CTLA-4. This sequence has been shown to be very efficient in facilitating protein transport not only into the ER, but from the ER to the Golgi apparatus. It enables even proteins which are blocked in their secretion pathway to bypass the ER retention mechanism. Alternative sequences may be used such as leader sequences, the ER retention sequence KDEL (SEQ ID NO:22) and the GPI anchor signal which promotes surface expression. The targeting protein should remain active in the presence of such additional sequences.

The nucleic acid vectors of the invention have a number of additional characteristics common to nucleic acid vectors in general.

The vectors may comprise a bacterial origin of replication to provide high copy numbers during production. An "origin of replication" is a nucleic sequence that initiates and regulates replication of nucleic acids, such as an expression vector. The origin of replication behaves as an autonomous unit of nucleic acid replication within a cell, capable of replication under its own control. Preferably, this origin of replication is derived from the pUC19 (Yanisch-Perron, 1985) backbone of pCMVβ and provides high copy numbers in E. coli.

The vector may further comprise a selection marker for selection in E. coli. This gene may be an antibiotic resistance gene or a gene involved in a metabolic pathway. Preferably, said gene is the asd gene of Salmonella typhimurium, which encodes aspartate β-semialdehyde dehydrogenase, an enzyme common to the biosynthetic pathways of lysine, threonine and methionine, as well as diaminopimelic acid, an essential constituent of the peptidoglycan cell wall of gram negative bacteria (Scleifer, 1972).

The nucleic acid vectors of the invention may also comprise a multiple cloning site to facilitate the cloning of antigens. The multiple cloning site contains a number of unique endonuclease restriction sites and is inserted in both directions.

The vectors may further comprise sequences to permit splicing and 3'polyadenylation of the transcript. Preferably, a fragment containing two introns used by SV40 to splice the viral 16S and 19S late mRNAs is placed upstream of the cloning site and a 196 bp fragment containing a late region polyA signal occurs downstream of the cloning site (Okayama, 1983).

The nucleic acid vectors may further comprise CG motifs which have an adjuvant effect, such as those described in WO 00/50075.

The functional prokaryotic and eukaryotic units (ori, selection marker, promoter, splice site and polyA signal) are preferably flanked by unique restriction sites, allowing their rapid removal and replacement or the introduction of additional elements for research or efficiency purposes, such as immunoregulatory sequences or genes.

A further aspect of the invention is a host cell comprising a vector or vectors of the invention as described above.

The vectors and compositions of the invention are primarily for use in nucleic acid vaccination. A further aspect of the invention is therefore a pharmaceutical composition comprising a therapeutically effective amount of the nucleic acid vector or vectors of the invention or compositions comprising said vectors in combination with pharmaceutically acceptable carriers.

The term "nucleic acid" includes DNA and RNA, and also their analogues, such as those containing modified backbones, and also peptide nucleic acids (PNA) etc.

By "therapeutically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trial's.

"Pharmaceutically acceptable carriers" include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants").

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Powell & Newman, 1995), containing 5% Squalene, 0.5% TWEEN 80 (polyoxyethylene sorbitan monooleate surfactant), and 0.5% SPAN 85 (sorbitan trioleate) formulated into submicron particles using a microfluidizer such as Model 110Y microfluidizer (Microfluidics, Newton, Mass.), (b) SAF, containing 10% Squalane, 0.4% TWEEN 80 surfactant, 5% PLURONIC L121 block polymer surfactant, and thr-MDP (see below) either microfluidized into a submicron emulsion or vortexed to generate a larger particle size emulsion, and (c) RIBI adjuvant system (RAS), (Ribi Immunochem, Hamilton, Mont.) containing 2% Squalene, 0.2% TWEEN 80 surfactant, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12, etc.), interferons (e.g. gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The pharmaceutical compositions (e.g. the polynucleotide vector(s), pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

A further aspect of the invention is a method of stimulating an immune response to a specific antigen or antigens by administering the vector(s), compositions or pharmaceutical compositions of the invention to a subject. The invention further provides the use of the pharmaceutical compositions, compositions and vector(s) of the invention in the manufacture of a medicament to stimulate an immune response against a specific antigen or specific antigens encoded by the vector or vectors.

Typically, the pharmaceutical compositions for use as vaccines are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect.

Liposomes that can act as nucleic acid delivery vehicles are described in U.S. Pat. No. 5,422,120, WO95/13796, WO94/23697, WO91/14445 and EP-524,968. As described in U.S. Ser. No. 60/023,867, nucleic acid sequences encoding a polypeptide can be inserted into conventional vectors that contain conventional control sequences for high level expression, and then be incubated with synthetic polynucleotide transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the nucleotide encoding the fusion protein under the control of a variety of tissue-specific or ubiquitously-active promoters.

The nucleic acid vectors of the invention can be adsorbed onto the surface of microparticles, in particular PLG microparticles, as described in WO98/33487.

The pharmaceutical compositions are conventionally administered parenterally, e.g. by injection, either subcutaneously, intramuscularly, or transdermally/transcutaneously (e.g. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

The vectors of the invention may also be administered as naked DNA. Exemplary naked DNA introduction methods are described in WO90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Other conventional methods for polynucleotide delivery that can be used for delivery of the vector(s) include, for example, use of hand-held particle gun, as described in U.S. Pat. No. 5,149,655; or use of ionizing radiation for activating transferred polynucleotide, as described in U.S. Pat. No. 5,206,152 and WO92/11033

Exemplary liposome and polycationic delivery vehicles are those described in U.S. Pat. Nos. 5,422,120 and 4,762,915; in WO 95/13796; WO94/23697; and WO91/14445; in EP-0524968; and in Stryer, 1975; Szoka, 1980; Bayer, 1979; Rivnay, 1987; Wang, 1987; and Plant, 1989.

Once formulated, the polynucleotide compositions of the invention can be (1) administered directly to the subject as described above; or (2) delivered in vitro.

The vectors and pharmaceutical compositions of the present invention have a use in vitro for producing increased yields of antibodies. As mentioned in the introduction, monoclonal and polyclonal antibodies are widely used in research and diagnostics. However, the production of such antibodies is often time consuming and depends on the purification of the protein in its native form. The vectors and pharmaceutical compositions of the current invention allow the production of antibodies to an antigen when the only information known about that antigen is its gene sequence. A further aspect of the invention is a method of stimulating an immune response to a specific antigen in vitro by administration of the vectors, compositions and pharmaceutical compositions of the invention. Antibodies obtained by the use of this method comprise a further aspect of the invention.

Generally, delivery of nucleic acids for in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

In addition to the pharmaceutically acceptable carriers and salts described above, the following additional agents can be used with pharmaceutical compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte; colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of plasmodium falciparum known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight, 1991; and Straubinger, 1983.

Liposomal preparations for use in the present invention include cationic (positively charged), anionic (negatively charged) and neutral preparations. Cationic liposomes have been shown to mediate intracellular delivery of plasmid DNA (Felgner, 1987); mRNA (Malone, 1989); and purified transcription factors (Debs, 1990), in functional form.

Cationic liposomes are readily available e.g. N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boehringer). Other cationic liposomes can be prepared from readily available materials using techniques well known in the art. See, e.g. Szoka, 1978; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See e.g. Straubinger, 1983; Szoka, 1978; Papahadjopoulos, 1975; Wilson, 1979; Deamer & Bangham, 1976; Ostro, 1977; Fraley, 1979; Enoch & Strittmatter, 1979; Fraley, 1980; Szoka & Papahadjopoulos,1978; and Schaefer-Ridder, 1982.

E. Lipoproteins

In addition, lipoproteins can be included with the polynucleotide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acid of these apoproteins are known and are described in, for example, Breslow, 1985; Law, 1986; Chen, 1986; Kane, 1980; and Utermann, 1984.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in Meth. Enzymol. 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in Pitas, 1980 and Mahey, 1979. Lipoproteins can also be produced by in vitro or recombinant methods by expression of the apoprotein genes in a desired host cell. See, for example, Atkinson, 1986. Lipoproteins can also be purchased from commercial suppliers, such as Biomedical Technologies, Inc., Stoughton, Mass., USA. Further description of lipoproteins can be found in Zuckermann et al. PCT/US97/14465.

F. Polycationic Agents

Polycationic agents can be included, with or without lipoprotein, in a composition with the desired polynucleotide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

In general, the practice of the invention will employ, unless otherwise indicated, conventional techniques of molecular biology, microbiology, recombinant DNA, and immunology, which are within the skill of the art. Such techniques are explained fully in the literature e.g. Sambrook, 1989; Glover, 1985; Gait, 1984; Hames & Higgins, 1984(a); Hames & Higgins 1984(b); Freshney, 1986; IRL Press, 1986; Perbal, 1984; the *Methods in Enzymology* series (Academic Press, Inc.), especially volumes 154 & 155; Miller and Calos, 1987; Mayer and Walker, 1987; Scopes, 1987, Weir and Blackwell, 1986.

Various aspects and embodiments of the present invention will now be described in some detail. It will be appreciated that modification of detail may be made without departing from the spirit and scope of the invention.

EXAMPLES

I) Construction of Pac-FN-NF

The mammalian reporter vector pCMVβ (Clontech, Palo Alto, Calif.) was digested with Not I to remove the β-galactosidase reporter gene. The linearized vector was purified from a 1% agarose gel using the Qiaex II gel extraction kit (Qiagen, Hilden, Germany) and religated with T4 DNA ligase, resulting in the vector pCMV-N. To introduce multiple cloning sites (MCS), oligonucleotides were generated using an ABI 394 DNA synthesizer (Perkin Elmer), using reagents from Cruachem (Glasgow), and purified following the manufacturer's instructions. Two oligomers of 71 nucleotides length (mcs1 and mcs2) (table 1) were annealed at equimolar conditions in T4 ligase buffer by heating to 70° C. for 5 minutes, slowly cooling down to 30° C., and a final chill on ice. The resulting double stranded MCS (MCS-FN/NF)) with 5'-GGCC-overhangs was inserted into the Not I site of Pcmv-N. the mcs1 oligomer was labeled with [γ-$^{32}$P]-ATP by polynucleotide kinase (New England Biolabs) and used to identify positive clones by colony hybridisation. Clones were tested for the direction of the MCS by restriction digestions. The resulting vectors were designated pCMV-FN and pCMV-NF. The pUC19 ori was amplified by PCR with sense primer ori1 and antisense primer ori2 (table 1) on pCMVβ, and the PCR product was digested with SalI and HindIII. The asd gene of *Salmonella typhimurium* was amplified by PCR with sense p;rimer ask1 and antisense primer asd2 (see table 1) on pYA3137, which was kindly provided by Roy Curtiss III, Washington University, St. Louis, Mo. The PCXR product was digested with HindIII and PstI. All PCR amplifications were carried out using a GeneAmp PCR System 2400 machine (Perkin Elmer) and using Pwo Polymerase (Boehringer Mannheim, Monza, Italy).

Both pCMV-FN and pCMV-NF were digested with PstI and SalI and the eukaryotic expression cassettes of 1086 basepairs (bp) length were purified from a 1% agarose gel. The digested PCR products ori (675 bp) and asd (1739 bp) were purified on MICROSPIN S400 HR columns and ligated to the 1086 bp fragments. The resulting plasmids are referred to as pAC-FN and pAC-NF (3500 bp). All unique restriction sites were tested by the corresponding restriction endonucleases and the polylinker sequence was confirmed using an ABI cycle sequencer.

II) Construction of pAC-AH

In a first step, a murine immunostimulatory sequence (ISS) of 30 bp length (Hartmann, 2000) was introduced into the HindIII site of pAC-FN. Annealing of the oligonucleotides iss1 and iss2 (table 2) results in a HindIII-compatible 5'-AGCT overhang. To facilitate screening, the HindIII site is eliminated upon insertion of the double stranded oligonucleotide, and a unique NheI site is introduced. The resulting plasmid of 3532 bp length was designated pAC-FN-ISS, and the news element was confirmed by sequencing.

In a second step, the V-like domain of mouse CTLA-4 was amplified by RT-PCR from splenocytes of a female C57BL/6 mouse. The cells were resuspended by passage through a Falcon 70 µm mesh size nylon cell strainer and further purified by a standard Ficoll gradient (lympholyte-M). $5 \times 10^6$ cells were cultured per well of a six-well tissue culture cluster (Costar) in 3 ml RPMI-1640, 2 mM L-glutamine, 100 units penicillin per ml, 100µ streptomycin per ml, 10% FBS, and 100 units of recombinant human interleukin-2 (Chiron) per ml for 24 hours at 37° C. and 9% $CO_2$ atmosphere. $40 \times 10^6$ cells were washed with PBS, and RNA was extracted using Trizol reagent (Gibco VRL), following the manufacturer's instructions. First strand cDNA was generated using components of the SUPERSCRIPT CHOICE system for cDNA synthesis (GibcoBRL). 2 µg of total RNA were annealed to 500 ng of oligo(dT)$_{12-18}$ primer. First strand synthesis was performed for 50 minutes at 42° C. with 200 units SUPERSCRIPT II reverse transcriptase in first strand buffer (0.1 M Dithiothreitol (DTT)-10 mM each dNTP). The enzyme was subsequently inactivated for 15 minutes at 70° C., and RNA was digested for 20 minutes 37° C. with 1 µg RNAse A. The V-like domain of mouse CTLA-4 was amplified by PCR with sense primer ctla41 and antisense primer ctla42 (table 2) using one tenth of the generated first strand cDNA as template, generating a fragment of 375 bp length.

In a third step, the mouse CTLA-4 domain was fused on the 5'-end to the tissue plasminogen activator (TPA) signal sequence and on the 3'-end via glycine linkers to the GCN4 leucine zipper and to a new MCS. This was achieved by overlapping PCR amplifications using the following (sense-antisense) primer pairs (table 2): fus1-fus2 (leading to a 443 bp product), fus3-fus4 (508 bp), fus5-fus-6 (575 bp), fus7-fus8 (633 bp), fus7-fus9 663 bp), and fus7-fus10 (697 bp). After each step, the PCR product was purified from 2% agarose gel. The final 697 bp product was cloned into the FseI and NotI sites of Pac-FN-ISS, and the resulting construct was designated Pac-AH. All unique restriction sites in pAC-AH were confirmed using the corresponding restriction endonucleases, and the new sequence between Fse and NotI was verified by sequencing.

III) Strains, Media, Growth Conditions, and DNA Preparation pCMVβ-derived constructs were transformed by electroporation and amplified in electrocompetent *Escherichia coli* (*E. coli*) XL1-Blue MRF' (Stratagene). Untransformed bacteria were grown in LB medium supplemented with 12.5 µg/ml tetracycline, for the selection of transformed bacteria 100 µg/ml ampicillin was added. pAC vectors were transformed and amplified in *E. coli* K12 6212 (Φ80d lacZ ΔM15 deoR Δ(lacZYA-argF) U169 sup E44 N gyrA recA1 relA1 endA1 ΔasdA4 Δ[zhf-2::Tn10] hsdR17 (r m$^+$, provided by R. Curtis III). Medium used for growth of untransformed bacteria was LB medium supplemented with diaminopimelic acid (DAP) at 50 µg/ml. After transformation by electroporation, bacteria were incubated at 37° C. for 30 minutes in SOC medium (Sambrook, 1989) supplemented with 50 µg DAP per ml, washed twice with SOC medium, and plated on LB agar for selection. Selected clones were grown in LB medium and large-scale preparations of supercoiled pAC-derived vectors were carried out either by the standard alkaline lysis procedure, two purification steps with cesium chloride-ethidium bromide gradients, n-butyl-alcohol extraction, iso-propyl-alcohol precipitation, and dialysis into TE buffer (Sambrook, 1989) or by the use of the ENDOFREE PLASMID MEGA kit for plasmid purification (Qiagen), following the suppliers protocol. DNA vaccines in TE buffer were ethyl-alcohol precipitated with sterile filtered 0.3 M sodium chloride for storage, and resuspended in endotoxin free PBS prior to immunization.

TABLE 1

Oligonucleotides used for the construction of pAC - FN/NF.

mcs1: 5'-GGCCGCACGCGTACTAGTGGGCCCGGGCGTACGCTTAAG
AATC
GATATCGGTACCAGATCTGAATTCGGCC-3'
(SEQ ID NO:1)

TABLE 1-continued

Oligonucleotides used for the construction of pAC - FN/NF.

mcs2: 5'-GGCCGGCCGAATTCAGATCTGGTACCGATATCGATTCTT
AAGC
GTACGCCCGGGCCCACTAGTACGCGTGC-3'
(SEQ ID NO:2)

ori1: 5'-ATCGTA*GTCGAC*GCGTTGCTGGCGTTTTCC-3'
(SEQ ID NO:3)

ori2: 5'-ATCGTA*AAGCTT*ATCCCTTAACGTGAGTTTTCG-3'
(SEQ ID NO:4)

asd1: 5' TACGC*CTGCAG*GGATCTTCCCTAAATTTAA-3'
(SEQ ID NO:5)

asd2: 5'-TACGC*AAGCTT*TCCAATTCAACATCAGGTA-3'
(SEQ ID NO:6)

Restriction sites in PCR primers used to assemble ori and asd to the eukaryotic expression box are underlined and in italics.

TABLE 2 oligonucleotides used for the construction of Pac-AH.

iss1: 5'-AGCTAGCTAGCAACGTCAGGAACGTCATGGAT-3'
(SEQ ID NO:7)

iss2: 5'-AGCTATCCATGACGTTCGACGTT*GCTAGCT-3'*
(SEQ ID NO:8)

ctla41: 5'-GCCATACAGGTGACCCAACC-3'
(SEQ ID NO:9)

ctla42: 5'-GTCAGAATCCGGGCATGG-3'
(SEQ ID NO:10)

fus1: 5'-GAAATCCAATGCCCGATTCAGAAGAGCCAGATCTGCCATACAGGTGACC-3'
(SEQ ID NO:11)

fus2: 5'-TGTTTCATGCGTCCACCGCCTCCTCCATCGATGTCACAATCCGGGC-3'
(SEQ ID NO:12)

fus3: 5'-TGTGGAGCAGTCTTCGTTTCGCCCAGCCAGGAAATCCATGCCCG-3
(SEQ ID NO:13)

fus4: 5'-TTTTCGAAAGAAGCTCTTCAACTTTATCTTCCAGCTGTTTCATGCGGTCC-3'
(SEQ ID NO:14)

fus5: 5'-AAGAGAGGGCTCTGCTGTGTGCTGCTGCTTGTGGAGCAGTCTTCG-3'
(SEQ ID NO:15)

fus6: 5'-TTTTTGAGGCGCGCAACTTCATTTTCGAGGTGGTGGTAGTTTTTCGAAAGAAAGAAGC-3'
(SEQ ID NO:16)

fus7: 5'-TAAATCAT*GGCCGGCC*GCCATGGATGCAATGAAGAGAGGCTCTGC-3'
(SEQ ID NO:17)

fus8: 5'-CCTCCACCACCGCGTTCACCAACAACAAGTTTTTTGAGGCGCGC-3'
(SEQ ID NO:18)

fus9: 5'-CTTCCAACTAGTCCTGAATTCCCGGGCCCGCTTCCAACTAGTCC-3'
(SEQ ID NO:19)

fus10: 5'-ATAGTTTA*GCGGCCGC*TTAACTATTCACTATAAGCTTCCAACTAGTCC-3'
(SEQ ID NO:20)

Sequences annealing in the first cycles of the overlapping PCR procedure are bold and underlined. Restriction sites used for screening (Nhe I in iss1 and iss2) and for cloning (FseI in fus7 and NotI in fus 10) are in italics and underlined.

REFERENCES

Armand et al (2000) *Vaccine* 18: 2212;
Atkinson et al (1986) *Annu Rev Biophys Chem* 15:403;
Barnhart et al (1998) *Hum. Gene Ther* 9:2545;
Bayer et al (1979) *Biochem Biophys Acta* 550:464;
Boyle et al (1998) *Nature* 392:408;
Breslow et al (1985) *Annu Rev. Biochem* 54:699;
Chaplin et al (1999) *Infect. Immun.* 67: 6434;
Chen et al (1986) *J Biol Chem* 261:12918;
Choo (1994) *Proc. Natl Acad. Sci. USA* 91: 1294;
Deamer & Bangham (1976) *Biochim. Biophys. Acta* 443:629;
Debs et al (1990) *J. Biol. Chem.* 265:10189-192;
Deliyannis (2000) *Proc. Natl Acad. Sci USA* 97: 6676;
Donnelly (1997) *Annu. Rev. Immunol* 15: 617;
Enoch & Strittmatter (1979) *PNAS USA* 76:145;
Felgner et al (1987) *PNAS USA* 84:7413-7416;
Fraley et al (1979) *PNAS USA* 76:3348;
Fraley et al (1980) *J. Biol. Chem.* (1980) 255:10431;
Freshney ed. (1986) *Animal Cell Culture;*
Fuller (1997) *Vaccine* 15:924;
Gait ed, (1984) *Oligonucleotide Synthesis;*
Glover ed. (1985) *DNA Cloning, Volumes I and ii;*
Greene (1996) *J. Biol. Chem* 271:26762;
Hames & Higgins eds. (1984a) *Nucleic Acid Hybridization;*
Hames & Higgins eds. (1984b) *Transcription and Translation;*
Hartikka (1996) *Hum. Gene Ther* 7:1205;
Hartmann (2000) *J. Immunol* 164:1617;
Heile (2000) *J. Virol* 74:6885;
Hug and Sleight (1991) *Biochim. Biophys. Acta.* 1097:1-17;
IRL Press (1986) *Immobilized Cells and Enzymes;*
Kane et al (1980) *PNAS USA* 77:2465;
Kwissa (2000) *Vaccine* 18:2337;
Law et al (1986) i *Adv. Exp Med. Biol.* 151:162;
Leitner (2000) *Vaccine* 18: 765;
Lew (2000) *Vaccine* 18:1681;
Linsley (1990) *Proc. Natl Acad. Sci. USA* 87: 5031;
Mahey et al (1979) *J Clin. Invest* 64:743-750.
Malone et al (1989) *PNAS USA* 86:6077-6081;
Mayer and Walker, eds. (1987), *Immunochemical Methods in Cell and Molecular Biology* (Academic Press, London);
Miller and Calos eds. (1987) *Gene Transfer Vectors for Mammalian Cells* (Cold Spring Harbor Laboratory);
Okayama (1983) *Mol. Cell Biol.* 3: 280;
Ostro et al (1977) *Biochem. Biophys. Res. Commun.* 76:836;
Papahadjopoulos et al (1975) *Biochim. Biophys. Acta* 394: 483;
Pardoll (1995) *Immunity* 3: 165;
Pennica (1983) *Nature* 301: 214;
Perbal (1984) *A Practical Guide to Molecular Cloning;*
Pitas et al (1980) *J. Biochem.* 255:5454;
Plant et al (1989) *Anal Biochem* 176:420;
Powell & Newman (1995) Chapter 10 in *Vaccine design: the subunit and adjuvant approach*, eds. Plenum Press;
Ramos (1999) *RNA* 5: 1374;
Rivnay et al (1987) *Meth Enzymol* 149:119;
Rosa (1996) *Proc. Natl Acad. Sci USA* 93: 1759;
Sambrook (1989) *Molecular Cloning; A Laboratory Manual, Second Edition*
Sato (1996) *Science* 273: 352;
Schaefer-Ridder et al (1982) *Science* 215:166;
Scopes, (1987) *Protein Purification: Principles and Practice*, Second Edition (Springer-Verlag, N.Y.);
Straubinger et al (1983) *Meth. Immunol.* 101:512;
Stryer (1975) *Biochemistry*, pages 236-240 W. H. Freeman, San Francisco;
Szoka & Papahadjopoulos et al (1978) *PNAS USA* 75:145;
Szoka et al (1978) *PNAS USA* 75:4194-4198;
Szoka et al (1980) *Biochem Biophys Acta* 600:1;
Ulivieri (1996) *J. Biotech* 51: 191;
Utermann et al (1984) *Hum Genet* 65:232;
Wang et al (1987) *PNAS USA* 84:7851;
Wang (1998) *Science* 282: 476;
Weir and Blackwell eds (1986) *Handbook of Experimental Immunology, Volumes I-I;V*
Wilson et al (1979) *Cell* 17:77;
Yanisch-Perron (1985) *Gene* 33:103;
Yew (1997) *Hum. Gene Ther.* 8: 575.

---

The invention claimed is:

1. A nucleic acid vector encoding a dimeric protein comprising a first fusion protein and a second fusion protein,
    wherein the first fusion protein comprises:
        (i) CTLA-4 or the V-like domain thereof,
        (ii) a leucine zipper domain, and
        (iii) a viral antigen;
    and wherein the second fusion protein comprises:
        (i) CTLA-4 or the V-like domain thereof,
        (ii) a leucine zipper domain, and
        (iii) optionally an antigen.

2. A nucleic acid vector encoding a fusion protein comprising:
    (i) CTLA-4 or the V-like domain thereof,
    (ii) a leucine zipper domain, and
    (iii) a viral antigen.

3. The nucleic acid vector according to claim 1 wherein an additional sequence selected from the group consisting of a nucleotide sequence encoding a secretory sequence, a nucleotide sequence encoding a leader sequence, and a nucleotide sequence encoding a retention sequence is fused to the nucleotide sequences encoding the first fusion protein or the second fusion protein.

4. A composition comprising two nucleic acid vectors according to claim 2, said vectors encoding a dimeric protein comprising a first fusion protein and a second fusion protein, wherein the first fusion protein comprises:
    (i) CTLA-4 or the V-like domain thereof,
    (ii) a leucine zipper domain, and
    (iii) a viral antigen;
and wherein the second fusion protein comprises
    (i) CTLA-4 or the V-like domain thereof,
    (ii) a leucine zipper domain, and
    (iii) optionally an antigen.

5. An isolated host cell comprising a nucleic acid vector according to claim 1.

6. A composition comprising the nucleic acid vector according to claim 1 or claim 2 and a suitable pharmaceutical carrier.

7. An isolated host cell comprising two nucleic acid vectors according to claim 1, each of said vectors encoding a dimeric protein comprising a first fusion protein and a second fusion protein, wherein the first fusion protein comprises:
    (i) CTLA-4 or the V-like domain thereof,
    (ii) a leucine zipper domain, and
    (iii) a viral antigen;
and wherein the second fusion protein comprises
    (i) CTLA-4 or the V-like domain thereof,
    (ii) a leucine zipper domain, and
    (iii) optionally an antigen.

8. The composition according to claim 4, further comprising a suitable pharmaceutical carrier.

9. The nucleic acid vector according to claim 2, wherein an additional sequence selected from the group consisting of a nucleotide sequence encoding a secretory sequence, a nucleotide sequence encoding a leader sequence, and a nucleotide sequence encoding a retention sequence is fused to the nucleotide sequence encoding the fusion protein.

10. The nucleic acid vector according to claim 3 or 9, wherein said additional sequence is selected from the group consisting of a nucleotide sequence encoding the human tissue-type plasminogen activator signal/pro sequence, a nucleotide sequence encoding the ER retention sequence KDEL (SEQ ID NO:22) and a nucleotide sequence encoding the GPI anchor signal.

11. The nucleic acid vector according to claim 1, wherein the first fusion protein or the second fusion protein comprises a GCN4 leucine zipper domain.

12. The nucleic acid vector according to claim 1, wherein the second fusion protein comprises a viral antigen.

13. The nucleic acid vector according to claim 2, wherein the fusion protein comprises a GCN4 leucine zipper domain.

14. The nucleic acid vector according to claim 4, wherein the first fusion protein or the second fusion protein comprises a GCN4 leucine zipper domain.

15. The nucleic acid vector according to claim 4, wherein the second fusion protein comprises a viral antigen.

16. The nucleic acid vector according to claim 7, wherein the first fusion protein or the second fusion protein comprises a GCN4 leucine zipper domain.

17. The nucleic acid vector according to claim 7, wherein the second fusion protein comprises a viral antigen.

* * * * *